United States Patent [19]

Norrlind et al.

[11] Patent Number: 5,445,811
[45] Date of Patent: Aug. 29, 1995

[54] ORGAN SPECIFIC EMULSION

[75] Inventors: Björn Norrlind; Arvid Wretlind, both of Stockholm, Sweden

[73] Assignee: Pharmacia AB, Sweden

[21] Appl. No.: 137,061

[22] PCT Filed: Apr. 22, 1992

[86] PCT No.: PCT/SE92/00261

§ 371 Date: Dec. 7, 1993

§ 102(e) Date: Dec. 7, 1993

[87] PCT Pub. No.: WO92/18169

PCT Pub. Date: Oct. 29, 1992

[30] Foreign Application Priority Data

Apr. 23, 1991 [SE] Sweden .................. 9101214

[51] Int. Cl.$^6$ .................................................. A61K 49/04
[52] U.S. Cl. ............................. 424/9.4; 424/195.1; 514/938; 514/943
[58] Field of Search .............. 424/5, 195.1; 128/654; 514/938, 943

[56] References Cited

U.S. PATENT DOCUMENTS

| | | | |
|---|---|---|---|
| 3,356,575 | 12/1967 | Arbaeus et al. | 167/95 |
| 4,192,859 | 3/1980 | Mackaness et al. | 424/5 |
| 4,280,996 | 7/1981 | Okamoto et al. | 424/199 |
| 4,404,182 | 9/1983 | Vermess et al. | 424/5 |
| 4,735,795 | 4/1988 | Robinson et al. | 424/5 |
| 5,234,634 | 8/1993 | Janoff et al. | 264/4.1 |
| 5,312,615 | 5/1994 | Schneider et al. | 424/5 |
| 5,318,767 | 6/1994 | Liversidge et al. | 424/4 |
| 5,318,768 | 6/1994 | Illig et al. | 424/5 |

FOREIGN PATENT DOCUMENTS

| | | |
|---|---|---|
| 294534 | 12/1980 | European Pat. Off. . |
| 676738 | 7/1952 | United Kingdom . |
| 721264 | 1/1955 | United Kingdom . |
| WO92/18168 | 10/1992 | WIPO . |

OTHER PUBLICATIONS

Reinig, et al., Liver Metastasis Detection: Comparative Sensitivities of MR Imaging and CT Scanning, Abdominal and Gastrointestinal Radiology, 1984, pp. 43–47.
Vermess, et al., Development and Experimental Evaluation of a Contrast Medium for Computed Tomographic Examination of the Liver and Spleen, Journal of Computer Assisted Tomography, 1979 3(1), pp. 25–31.
Davis, et al., Lipid Emulsions as Drug Delivery Systems, Annals of the NY Acad. Sci., 1987, vol. 507, pp. 75–88.
Miller, et al., CT of the Liver and Spleen with EOE-13: Review of 225 Examinations, Am. J. Roent., 1984, 1984, pp. 235–243.
Schumacher, et al., Experimental Data on the Problem of Specific Hepatosplenography with Radiodense Lipomicrons, Europ. J. V. Radiology, 1985, vol. 5, pp. 167–174.
Grimes, et al., Formulation and Evaluation of Ethiodized Oil Emulsion for Intravenous Hepatography, J. V. Pharmaceutical Sci., 1979, vol. 68, No. 1, pp. 52–56.
Thomas, et al., Hepatolienography: Past, Present, and Future, Radiology, 1951, pp. 669–684.
Maranhao, et al., Effects of Cholesterol Content on the Metabolism of Protein–Free Emulsion Models of Lipoproteins, Biochimica et Biophysica Acta 875 (1986), pp. 247–255.

*Primary Examiner*—Gary E. Hollinden
*Attorney, Agent, or Firm*—Pollock, Vande Sande & Priddy

[57] ABSTRACT

Disclosed are emulsions for intravenous administration based on lipophilic iodized and/or bromated substances with emulsifiers and containing derivatives of cyclopenta-phenanthrene, wherein the weight ratio between emulsifier and derivative in the emulsion is between 10:1 and 1:2. These emulsions are intended for use as X-ray contrast agent, particularly for visibilizing the presence of tumors, metastases and the like in liver and spleen. The derivative of cyclopenta-phenanthrene is preferably cholesterol, phytosterol, sitosterol, sigmasterol and/or campesterol. The invention also relates to a method for preparing the emulsion and to the use of the emulsion in the preparation of an X-ray contrast medium for computed tomographic examinations.

19 Claims, 2 Drawing Sheets

ORGAN SPECIFIC EMULSION

This application is a 371 of PCT/SE92/00261 filed Apr. 22, 1992.

The present invention is related an emulsion intended essentially for intravenous administration as a contrast agent for visibilizing the presence of tumours, metastases and the like in the liver and spleen of a patient. The emulsion is characterized in that it contains a lipophilic iodized and/or bromated substance which is emulsified as an oil-in-water emulsion with the aid of emulsifiers, for instance mixtures of phospholipids and derivatives of cyclopenta-phenanthrene (steroids), in particular sterols. The emulsion can be autoclaved, is highly stable and has a mean parfide size of smaller than 1 $\mu$m. This contrast agent is characterized by its very high affinity to liver and spleen, this affinity being about three times greater than the affinity of earlier known contrast emulsions of the same particle size.

The addition of steroids, and then particularly the addition of phytosterols or cholesterol to the oil phase of iodized or bromated organic substances in emulsion form in accordance with this patent application enables the particles in the emulsion to be directed specifically to liver and spleen, subsequent to being administered intravenously. The inventive emulsion therewith fulfils all the requirements that can be placed on an organ specific contrast agent intended for computed tomography.

INTRODUCTION

Various emulsions containing iodized fat have earlier been produced for use as a contrast agent. These iodine-containing fat emulsions have been found to afford advantages that are not afforded with water-soluble X-ray contrast media. For instance, the iodine-containing fat emulsions are characterized by a low osmotic pressure, among other things. This is particularly benefidal in the case of intravenous administration, since it reduces injury to the endothelial tissue and also reduces the occurrence of thrombophlebitis.

Iodine-containing fat emulsions have been the subject of particular interest, because the emulsion particles were taken-up into the cells of the reticuloendothelial system (RES-cells). This observation was made as early as 1930, by W. S. Keith, D. R. Brigys (Proc. Soc. Exp. Biol. Med. 27: 538, 1930). This enabled liver and spleen with large quantities of RES-cells to be made more radio-opaque than other tissues. However, it is only recently that it has been possible to utilize this property of the iodine-containing emulsions, due to the development of more sensitive methods of X-ray examination utilizing so-called computed tomography. This has made it possible to improve radiological examinations on the liver, for instance, so that small tumours, metastases, abscesses, etc. in the liver can be observed more readily. One reason for this is that the RES-cells in the liver which take-up the emulsion droplets are not found in tumour tissue. Consequently, because the tumours do not take-up the contrast agent, they are seen as "voids" in the image obtained with computed tomography. Because of the improved X-ray diagnosis made possible in this way, different methods of producing iodine-containing fat emulsions for intravenous injection have been investigated intensely over recent years.

A Summary is given in the following of earlier publications, patent specifications and patent applications which relate to iodine-containing fat emulsions for intravenous use and intended particularly for X-ray examination of liver and spleen.

1. Roth, Stephan. "Röntgenkontrastmittel auf der Basis einer Emulsion von jodierten ölen". Patent Specification DE 26.02.907 (27.1.76). The invention relates to an emulsion (oil-in-water) which contains iodized triglyceride. The emulsion is characterized in that it contains 50–60% of an iodized triglyceride and 2–10% of polyoxyethylene-sorbitan fatty add esters as emulsifier. The resultant emulsion can only be sterilized by gamma radiation. The emulsion is intended for use with lymphangiography and hepatosplenography.

2. Grimes, George and associates. "Formulation and Evaluation of Ethiodized Oil Emulsion for Intravenous Hepatography". Journal of Pharmaceutical Sciences 68: 52–56, 1979. The authors have produced various emulsions with iodized oil and have studied the effects of these emulsions on rabbits and monkeys. This study was made with the view of investigating the possibility of sterilizing the emulsions. It was not possible to heat sterilize the emulsions by autoclaving. Consequently, a method was developed which involved separate sterile filtration of both the iodized oil and of the aqueous solutions of the emulsifiers used. The emulsions were then homogenized aseptically. The emulsifiers investigated were polysorbat 80, sorbitan monooleate and phosphatidylcholine. According to the authors, only those emulsions which had a particle size of 2–3 $\mu$m in diameter were found suitable as contrast agent for liver diagnosis. The emulsions were considered unusable as contrast agent when the mean particle size was less than 0.75 $\mu$m in diameter.

3. Vermess, Michael, et al. "Development and Experimental Evaluation of a Contrast Medium for Computed Tomographic Examination of the Liver and Spleen". J. Comput. Assist. Tomogr. 3: 25–31, 1979. The authors describe several iodine-containing fat emulsions of varying compositions. The emulsion which was considered to be the best of those prepared was designated EOE-13 and contained 53% v/v iodized fat (Ethiodol), 10% alcohol, 0.45% soy bean lecithin and phosphate buffer adjusted to pH 7. About 55% of the oil was present in the form of particles having a diameter of 1–3 $\mu$m. These authors also maintained that it was also necessary for the particles to have a size essentially in the range of from 2–4 $\mu$m in order for the emulsion to be taken-up into the liver in sufficient quantities 4. Donald Miller and associates. "CT of the Liver and Spleen with EOE-13: Review of 225 Examinations". (Amer. J. Roentgenol. 143: 235–243, 1984) have published a large number of examinations of the liver performed with infusion of the aforesaid preparation EOE-13. The computed tomographic results were excellent and it was possible to show the presence of tumours and metastases in several patients. The infusions, however, resulted in a number of side effects, among them pyrexia, shivering fits and headaches.

5. Vermess, Michael, et al. "Ethiodized Oil Emulsion or lntravenous Hepatography". U.S. Pat. No. 4,404,182, Sep. 13, 1983. This patent relates to the preparation of iodized fat emulsions with lecithin as emulsifier. According to this patent the emulsion is prepared such that 30–35% by volume of the particles will have a diameter of 2–3 $\mu$m. Because the emulsion is unable to withstand heat sterilization (autoclaving), it is necessary to sterilize the emulsion by filtration. The emulsion is said to be intended for use with animals, preferably rabbits and monkeys.

6. Schumacher, K. A., et al. (Europ. J. Radiol. 5: 167–174, 1985) reports experiments carried out with a large number of different emulsions containing iodized fat. The emulsions were prepared with several different emulsifiers, such as polyoxyethylene-4-sorbitan-monolaurate, Hydrophilic Lipophilic Balance (LBL) 12,1 (Tween 21 Atlas Chemie), polyoxyethylene-20-sorbitan monoleate HLB 15,3 (Tween 80, Serva), glycerol polyethylene glycolridnoleate, HLB 14,5 (Cremophor EL), diacetylphosphate DP (Sigma), lecithin from eggs (Fluka GmbH), Doxypolygelatin (Gelinfundol 5.5% Biotest GmbH) and dextran 60 (Macrodex 4.5% RL Knoll). Emulsions with varying droplet sizes were prepared with iodized fat and the aforesaid emulsifiers. The resultant emulsions (the lipomicrons) were found to be unstable when heat sterilized. The emulsions were therefore kept sterilize by adding a "P.S.N. antibiotic mixture". When injected intravenously in rats and dogs, several of the emulsions prepared resulted in a drop in blood pressure. Experiments showed that the different lipomicrons were taken-up in the liver and spleen to varying degrees, among other things because of the size of the fat particles.

7. Reinig, James, et al. (Radiology 162: 43–47, 1987) have used emulsion EOE-13 (mentioned under item 3 above) to visualize the liver by computed tomography. It is stated in the report that the emulsion used had a particle size of 1–4 μm. The emulsion EOE-13 is prepared from iodized ethyl ester of fatty adds from poppy seed oil. When examining the liver, the emulsion was applied in an amount of 0.25 ml/kg over the course of one hour. The authors reported that EOE-13 was an unstable emulsion and difficult to produce in large quantities. EOE-13 also has produced side effects (pyrexia and shivering fits).

8. Farbenfabriken Bayer. GB Patent 676,738 describes an emulsion containing iodized oils or iodized fatty add esters and synthetic nonionic emulsifiers. Thiosulphate is added to the preparation, to counteract side-effects. The preparations are semi-solid at room temperature, and must therefore be heated. to 37° C. prior to being injected. Nothing is said with regard to the stability of the preparation when heat sterilizing the same.

9. Astra. GB 721,264. This patent relates to preparations of an X-ray contrast medium which is dissolved or dispersed in water and to which a viscosity-elevating agent is added in order to bring the relationship between the "dynamic viscosity" of the preparation and its density, i.e. the "kinematic viscosity", to the same order of magnitude as that of blood, which is said to impart to the preparation flow properties which are similar to those of blood. Nothing is said of the methods used to sterilize the preparations.

10. Leo. U.S. Pat. No. 3,356,575 (corresponds to GB 1,070,517 and SE 337 655). This patent relates to autosterile X-ray contrast media containing iodized vegetable oil or iodized ester of vegetable oil in the form of an anhydrous emulsion of glycerol and lecithin. The preparation is a concentrate which must be diluted with sterile water prior to injection. It is reported in the text that a concentrate has been chosen because when diluted with water an undesirable aggregation of the particles and the hydrolysis of the fat to form free fatty acids and iodide takes place. It has not been found possible to heat sterilize the diluted emulsion.

According to Example 8 of this patent specification, the diluted emulsion contains 18% glycerol and 18% oil, the glycerol content thus being eight times that of a glycerol solution isotone with blood. An osmotic pressure of this magnitude is unacceptable in the case of a solution, which is injected directly into the blood stream.

The aforesaid emulsions containing iodized fat are encumbered with a number of drawbacks. For example, it has not been possible to produce emulsions with iodized oil which have a particle size beneath 0.5 μm, this particle size being necessary m order to obtain a stable emulsion; which are stable after being heat sterilized by autoclaving; which have satisfactory stability when stored for long periods; and which do not contain synthetic emulsifiers such as Tween and Span, these substances producing serious side effects.

11. U.S. Pat. No. 4,917,880 (K.A.J. Wretlind and Bengt Ajaxon) teaches a method of producing an iodine-containing emulsion (Intraiodol ®) with which the aforesaid drawbacks are avoided. Intraiodol ® contains 10% (V/V) Ethiodized Oil Injection USP and 1.2% purified egg phospholipids in an aqueous phase with 2.25% glycerol and 0.1% phenylalanine. The invention is based on the concept of producing a fat emulsion containing iodized fat and exhibiting good stability, both when autoclaving and when stored for long periods, and which also exhibits good clinical tolerance when injected intravenously, by the suitable additions and use of egg yolk phospholipids as emulsifiers. An emulsion which has been prepared in accordance with this invention also has the desirable property of being taken-up into the liver and the spleen. It has also been found that an emulsion of this kind is taken-up solely in healthy liver tissue and not into tumour tissue.

This emulsion has been used in examining the livers of 16 patients using computed tomographic techniques. It was found that the emulsion is well-suited for visualizing tumourous tissue in the liver. Earlier emulsions containing iodized fat have been taken-up in the reticuoendothelial cells (RES-cells) of the liver, which has been considered desirable and possible to achieve by utilizing the ability of these cells to take-up, from the blood, large particles which are recognized as being foreign to this cell system. The emulsion described by Wretlind and Ajaxon is characterized, however, in that the particles are not taken-up in the RES-cells but are instead taken-up in the space of Disse and in hepatocytes. The space of Disse is a compartment between the endothelial cells of the vessel wall and the hepatocytes (the liver cells) which communicate with the blood vessel through small windows (fenestrae) in the vessel wall. The reason for this difference in uptake is probably to be found in the particle size. The earlier emulsions had a particle size of 1–3 μm, which explains the uptake in RES. The emulsion to Wretlind and Ajaxon has much smaller particles (0.1–0.3 μm). Such small particles are not taken-up by RES.

The iodine-containing fat emulsion according to Wretlind and Ajaxon has certain advantages over the emulsions described under items 1–10 above. One of the most important of these advantages is that the burden represented by the quantity of organically-bound iodine that is taken-up in the individual cell is much smaller, since the number of hepatocytes in the liver is from 9–10 times greater than the number of RES-cells. The same total quantity of iodine is required in the liver for the desired contrast effect in both of said cases. One drawback, on the other hand, is that the uptake of Intraiodol ® in the liver is only about ⅓ of the amount that is administered intravenously.

BACKGROUND OF THE INVENTION

The properties required of an X-ray contrast medium in order to visualize liver and spleen are recited in a publication by Thomas, S. F. and associates (Hepatolienography: Past, Present and Future. Radiology 57: 669–684, 1951). According to Thomas and associates such a contrast medium 1. shall have only slight acute or chronic toxicity or none at all;
2. shall not be radioactive;
3. shall contain elements of sufficiently high atomic number to provide a satisfactory X-ray density even when administered in moderate quantities;
4. shall be capable of being administered intravenously without difficulty;
5. shall have a high affinity for selective uptake in the liver and the spleen; and
6. shall secrete quickly and positively from the body.

It is evident from the works discussed in the aforegoing that several of these requirements have already been satisfied. The most serious problem still to be resolved is that of producing an emulsion of X-ray contrast agent which has small particle sizes and with properties which will enable the major part of the high-affinity emulsion particles to be taken-up selectively and evenly in the liver and the spleen.

The possibility of preparing emulsions which contain fat-soluble pharmaceuticals which are specifically taken-up by different body organs has attracted great interest since such emulsions were first prepared for intravenous injection about 20 years ago. In a summary, 1987, in the book "Biological Approaches to the Controlled Delivery of Drugs", (Annals of the New York Academy of Sciences, Vol. 507, Dec. 22, 1987: Lipid Emulsions as Drug Delivery Systems; S. S. Davies, et al, pages 75–88), there is discussed the possibility of directing the particles in fat emulsions to specific organs. Despite the fact that several possibilities of steering or directing the emulsion particles to different organs have been investigated, it is obvious that no important scientific or commercial advance has been made in this direction up to the present time.

The investigations carried out hitherto have shown that an emulsion which contains large particles is taken-up in the RES-cells of the liver and that, on the other hand, an emulsion which contains small particles is taken-up in the space of Disse and in the hepatocytes. It has been discovered that about 80% of the iodine-containing fat injected is taken-up by the liver when using an emulsion having a particle size of 1–3 $\mu$m. On the other hand, only about ¼–⅓ of the organically bound iodine is taken-up by the liver from an emulsion, which has a particle size of 0.1–0.3 $\mu$m. It has become desirable to produce a stable iodine-containing emulsion with small particles that is taken-up by the liver to the same high extent as an iodine-containing emulsion with large particles. Hitherto, it has been considered impossible to produce an emulsion with such properties. In endeavours to control the liver uptake of an emulsion of iodized fat of small particle size, we have tested a large number different emulsion additives. Quite surprisingly, we discovered that this control could be achieved with certain additives, despite the particle size of the emulsion being so low as to render negligible any expectation of the emulsion being taken-up into the RES-system of the liver. Thus, as a result of the present invention, we have successfully prepared an iodine-containing fat emulsion which is stable, which can be autoclaved and which fulfils the requirements stated by Thomas and associates in a far better way than do earlier known iodine-containing fat emulsions.

DESCRIPTION OF THE INVENTION

Figure 1:
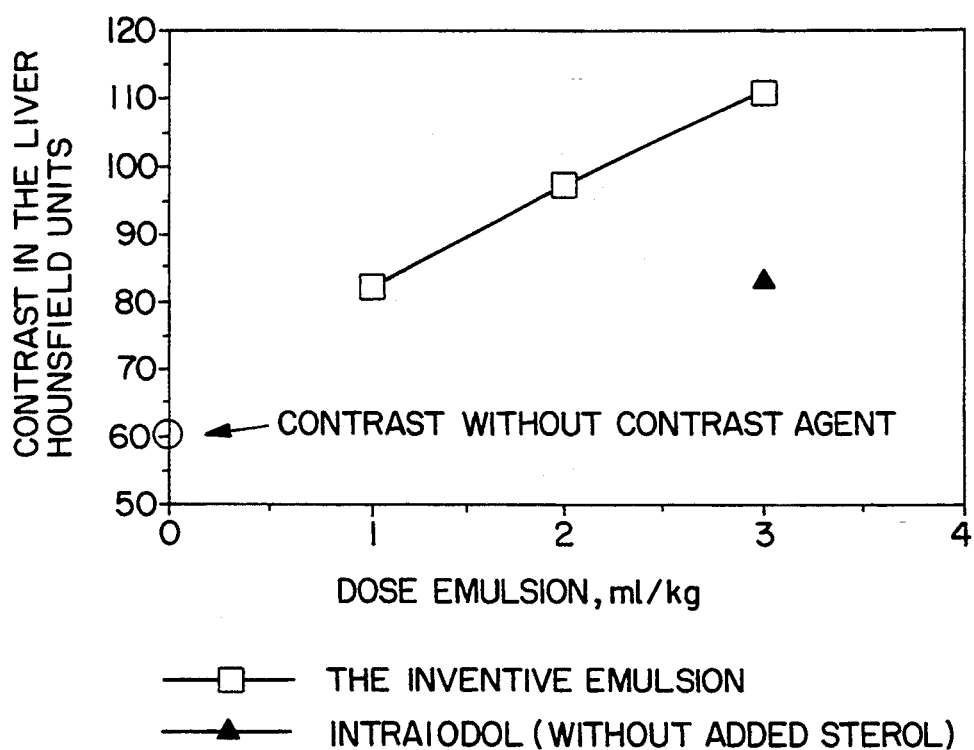
FIG. 1 illustrates contrast (measured as Hounsfield units) in the livers of rats which have been administered with Intraiodol ® (without cholesterol additives) and an inventive emulsion in different dosages.

As a result of comprehensive experimental work, we have been successful in showing that emulsions based on lipophilic (fat soluble) iodized and/or bromated substances with small particles can be prepared in a manner such as to achieve almost total uptake of the emulsion particles in the liver and the spleen. This has been found to be possible solely by choosing suitable additives in the emulsion system used.

This invention is of the greatest importance, primarily because it enables the amount of iodine-containing and/or bromine-containing substance administered to the organism to be reduced to about 30% of the quantity used in earlier developed contrast emulsions.

The present invention relates to emulsions for intravenous injection, based on lipophilic iodized and/or bromated substances, and with emulsifiers which contain a derivative of cyclopenta-phenanthrene, wherein the weight ratio between emulsifier and cyclopenta-phenanthrene derivative in the emulsion is between 10:1 and 1:2, preferably between 2:1 to 1:1.

The derivatives of cyclopenta-phenanthrene is also designated steroids and the derivative used is preferably a sterol such as cholesterol, phytosterol, sitosterol, sigmasterol and/or campesterol. Emulsifiers may preferably be phospholipids, which normally occur as mixtures of closely related chemical compounds, when isolated from natural sources.

Naturally, other types of emulsifiers and mixtures of emulsifiers may also be used. Synthetic emulsifiers of the type normally used for preparing oil-in-water emulsions are of particular interest in this case.

Examples of lipophilic iodized substances are iodized glycerides produced, for instance, from poppy seed oil, soybean oil, olive oil, palm oil, teaseed oil, castor oil, sesame oil, grapeseed oil, rape oil, walnut oil, corn oil, kapok oil, rice bran oil, peanut oil, cottonseed oil, sunflower oil, safflower oil, menhaden oil, salmon oil, herring oil, lard or other vegetable or animal oils. Ethyl esters of fatty acids which can be used either alone or in combination with iodized glycerides according to the present invention subsequent to being iodized can be obtained from the aforesaid fats. Esters of pure fatty acids may also be used. Examples are ethyl esters of triiodostearic acid and ethyl ester of monoiodostearic acid, this latter having the advantage of that it can easily be produced in a relatively pure state by molecular distillation. Esters of other fatty acids capable of being iodized are suitable, provided that a satisfactory X-ray density can be achieved. The lipophilic substance may comprise iodized glycerides and/or iodized esters of fatty acids, in an amount of 1–50%, preferably 5–20%.

An important property of emulsions prepared from iodized triglycerides is the excellent biological tolerance, which is observed when the emulsions are administered intravenously. It makes them especially suitable as contrast emulsions for the liver and the spleen. However, a sufficient degree of physical and chemical stability of these emulsions can sometimes be difficult to attain.

Other lipophilic iodized substances can be used, such as lipophilic substances that contain an iodized benzene ring. One example is Iophendylate (CAS 99-79-6) containing a monoiodo-benzene group.

Bromated organic substances, such as bromated ethyl esters of fatty acids, or bromated perfluoro compounds may also be used. Mixtures of different lipophilic iodized and/or bromated substances may also be used, of course.

The emulsion may also contain 1–50%, preferably 5–20% vegetable or animal oil. The addition of non-iodized glycerides are of special interest since emulsions with such additions have special and advantageous properties as regard to the chemical and physical stability and biological tolerance.

Other lipophilic, pharmacologically active substances, or substances for diagnostic use may be added to the emulsion of iodized and/or bromated lipophilic substance, and then especially those substances which it is desired to deliver specifically to the liver and the spleen.

Additional substances may also be added to the aqueous phase of the emulsion. In order to further improve the stability of the emulsion during preparation and storage by stabilizing the pH of the emulsion, minor quantities of buffer substances may be added, for instance in the form of salts of preferably monovalent weak bases or weak adds, such as salt of triethanol amine or salt of acetic add. Amino acids or their salts may also be used, such as phenylalanine, alanine, isoleucine, leucine, serine and/or taurine. The emulsion may also contain one or more of the following compounds or salts thereof in a concentration of 0.1–5%: Glycerol, pelargonic acid, oleic add, linolenic acid, carbamide and E-vitamin or other fat-soluble vitamins. The mean size of the emulsion particles will preferably be beneath 1 μm.

The emulsion is prepared in accordance with conventional methods known to those persons skilled in this art, by mixing the aqueous phase with the lipophilic iodized and/or bromated substance and the optional additional fat or oil, the emulsifiers used, derivatives of cyclopenta-phenanthrene, optional auxiliary substances and/or stability enhancing compounds.

One example of the mixing method used involves dissolving phospholipids and derivative of cyclopenta-phenanthrene in the lipophilic iodized substance, and adding this oil phase to an aqueous phase containing desired water-soluble additives, while vigorously stirring the mixture at elevated temperature. The emulsion is then brought to the desired particle size, preferably by homogenizing the mixture in a homogenizer of suitable construction, for example under high pressure in a so-called valve homogenizer. The resultant emulsion is sterilized, preferably by autoclaving the emulsion in its final package form (normally glass bottles).

Sterile filtration of the emulsion followed by aseptic pouring of the emulsion into its package form is a conceivable alternative method.

The invention also relates to the use of these emulsions in the preparation of an X-ray contrast agent for computed tomographic examination of body organs, particularly of the liver and the spleen.

We have found sterols, such as cholesterol and phytosterols to be particularly suitable derivatives of cyclopenta-phenanthrene. One advantage with the use of these steroids is that they are well known, biologically tested and tolerable. Phytosterols are normally included in foodstuffs, primarily in oils of vegetable origin.

The daily intake of cholesterol through the food chain varies from 0.2 to 2 g, and the liver also has a high capacity of synthesizing cholesterol when the oral intake of cholesterol is low. Normally, lipoproteins in the blood are responsible for transporting cholesterol to the various organs of the body and for retransporting cholesterol to the liver. A major part of the cholesterol is converted to bile adds in the liver. Cholesterol and bile adds are thereafter excreted via the gall.

It is known to use as emulsifiers for iodized fats phospholipids produced from natural sources, such as egg yolks or vegetable oils Pure, chemically well-defined phospholipids can also be produced by chemical synthesis. In the preparation of egg phospholipids, lipids are fractionated from egg yolk, mainly triglycerides and cholesterol being removed. Despite this, the prepared emulsifier will nevertheless contain small quantities of cholesterol (typical in a weight ratio phospholipids/-cholesterol of 50/1), this cholesterol presence rather having the nature of a contaminant or impurity in the phospholipid mixture. It is not until the phospholipid mixture contains substantially higher concentrations of sterols, however, that an increased specificity for liver uptake and spleen uptake of a contrast emulsion in which the phospholipid mixture is included can be noticed.

As a result of carrying out comprehensive experiments, we have discovered that the affinity of the emulsion to liver and to spleen is greatly enhanced when a sterol is added in a quantity which is half as great or equal to the amount of phospholipid present (weight ratio phospholipids/cholesterol 2:1 to 1:1). The stability of the emulsion, however, is impaired when the amount of cholesterol is increased to an amount in which the ratio of phospholipids to cholesterol is 1:2. The choice of derivative of cyclopenta-phenanthrene as a means for enhancing the specificity of an emulsion with iodized and/or bromated substance for uptake in the liver is of great importance, since in addition to increasing the specificity for uptake of the emulsion particles they may also be pharmaceutically active in liver tissue. For instance, there are found in the steroid group many important substances (fusidic add, fluocortisone, betametasone, cortisone, hydrocortisone, methylprednisone, prednisolone, prednylidene, triamdnolone, etc.) where a specific uptake to liver tissue would be extremely valuable.

Another important aspect of the invention resides in the possibility of dissolving fat-soluble pharmaceuticals in the lipophilic part of the iodized and/or bromated fat emulsion. Because the fat emulsion is taken-up specifically and rapidly in the liver and the spleen, there is obtained hereby a method which directs fat-soluble pharmaceuticals specifically to these body organs.

Furthermore, fat-soluble contrast agents can also be used with another active mechanism. An example of such means is perfluorooctylbromide, which has been suggested as a diagnostic medium for use with computed tomography, sonography or for imaging with magnetic resonance (MR). This is reported in the work: "Potential Role of Perfluorooctylbromide in the Detection and Characterization of Liver Lesions with CT" (Robert F. Mattrey: Radiology Vol. 170, No. 1, 18–20, 1989).

Our invention enables emulsions of lipophilic iodized and/or bromated substances to be obtained which have very high stability in autoclaving and storage. This distinguishes our emulsion from many earlier iodized fat emulsions which cannot be heat sterilized.

As a result of the described invention, we have successfully prepared an emulsion of iodized and/or bromated fat for X-ray diagnostic use, with very high specificity to the liver and spleen, based on a novel principle in the present context, namely the principle of directed emulsion uptake in liver tissue where a predominant part of the emulsion particles is taken-up in the space of Disse and in the hepatocytes, as illustrated experimentally in Example 18 below.

This avoids possible side effects through a large uptake in the RES-cells of these organs, while enabling the requisite dose for contrast amplification to be greatly reduced, therewith greatly reducing the risk of side effects.

In this way, the object is reached of obtaining a safe contrast medium which is free from side effects and which can visibilize tumours and metastases in liver and spleen with the aid of computed tomography.

EXAMPLES OF PREPARATIONS

EXAMPLE 1

A mixture of the following ingredients was prepared.

| Iodized ethyl esters of fatty acids from poppy seed oil | 10 ml |
|---|---|
| Phenylalanine | 0.1 g |
| Phospholipids from egg | 1.2 g |
| Cholesterol | 1.2 g |
| Glycerol | 2.25 g |
| Sterile water | to 100 ml |

An aqueous phase was prepared by mixing glycerol and phenylalanine with the sterile water and heating the solution to 70°–80° C. An oil phase was prepared by dissolving the phospholipids and cholesterol in the iodized ethyl esters while carefully heating the system to 50° C. within a nitrogen gas shield. The oil phase was added slowly to the aqueous phase while vigorously stirring the mixture with an intensive mixer type Ultraturrax. The pH of the mixture was adjusted with diluted NaOH and the mixture then homogenized in a valve homogenizer under high pressure. The homogenized mixture was then dispensed into glass bottles and then autoclaved. The mean particle size of the prepared emulsion was measured to 0.25 μm and the iodine content was measured to 4.2% organically bound iodine. After three months storage at room temperature, the mean particle size was generally unchanged at 0.23 μm. This proves that the emulsion is stable after being heat sterilized and stored at room temperature.

EXAMPLE 2

A mixture was prepared from the following substances.

| Iodized soybean oil | 2.5 ml |
|---|---|
| Leucine | 0.1 g |
| Soybean oil | 7.5 g |
| Phospholipids from soy beans | 1.2 g |
| Cholesterol | 0.6 g |
| Glycerol | 2.25 g |
| Sterile water | to 100 ml |

The aforesaid mixture was homogenized and the resultant emulsion then autoclaved at 121° C.

Example 3

A mixture was prepared from the following substances.

| Ethiodized Oil Injection USP XXII | 10 ml |
|---|---|
| Phenylalanine | 0.1 g |
| Phospholipids from egg | 1.2 g |
| Cholesterol | 1.2 g |
| Glycerol | 2.25 g |
| Sterilized water | to 100 ml |

The mixture was homogenized and the resultant emulsion autoclaved at 117° C. The mean particle size was measured to 0.27 μm. The emulsion was then shaken for 24 hours and the mean particle size then measured to 0.26 μm. The suspension was then frozen to a temperature of −18° C. and then thawed, whereafter the mean particle size was measured to 0.28 μm. This proved that the emulsion had satisfactory stability.

Example 4

A mixture was prepared from the following substances.

| Iodized ethyl esters of fatty acids from poppy seed oil | 10 ml |
|---|---|
| Phenylalanine | 0.1 g |
| Phospholipids from egg | 1.2 g |
| Phytosterols* | 1.2 g |
| Glycerol | 2.25 g |
| Sterile water | to 100 ml |

(*Sigma, St. Louis, MO, U.S.A.: S-5753 containing b-sitosterol, campesterol and dihydrobrassicasterol).

The mixture was then homogenized and the emulsion then autoclaved, whereafter the mean particle size was measured to 0.34 μm and the iodine content was measured to 4.7% organically bound iodine.

Example 5

A mixture was prepared from the following substances.

| Ethiodized Oil Injection USP XXII | 10 ml |
|---|---|
| Phenylalanine | 0.1 g |
| Phospholipids from egg | 1.2 g |
| Cholesterol | 0.3 g |
| Glycerol | 2.25 g |

| | |
|---|---|
| Sterile water | to 100 ml |

The mixture was homogenized and the emulsion then autoclaved, whereafter the mean particle size was measured at 0.27 μm.

Corresponding emulsions were prepared with 0.6 and 1.2% cholesterol respectively, these emulsions having a mean droplet size of respectively, 0.21 and 0.27 μm after being autoclaved.

Example 6

A mixture was prepared from the following ingredients

| | |
|---|---|
| Ethiodized Oil Injection (USP XXII) | 10 ml |
| Purified Soybean oil | 10 ml |
| Phospholipids from egg | 1.8 g |
| Cholesterol | 1.5 g |
| Phenylalanine | 0.1 g |
| Glycerol | 2.25 g |
| Water for injection | to 100 ml |

A water phase was prepared by mixing of glycerol and phenylalanine with water for injection and heating of the solution to 70°-80° C.

A lipid phase was prepared by mixing of the Ethiodized Oil Injection and soybean oil, to which the phospholipids and cholesterol was added and dissolved under agitation and cautious heating, protected with nitrogen. The lipid phase was slowly added to the water phase under vigorous mixing with a mixer type Ultraturrax. After adjustment of the pH with diluted NaOH, homogenization was performed in a valve homogenizer under the pressure. After dispersing on glass bottles the emulsion was heat sterilized at 117° C. The mean particle size of the emulsion was determined to be 0.33 μm.

Example 7

An emulsion was prepared in the same manner as described in Example 6. However, instead of soybean oil was used a purified olive oil in the same amount. The mean particle size of the emulsion was determined to 0.35 μm. The level of iodide in the autoclaved emulsion was 544 ppm.

Example 8

An emulsion was prepared in the same manner as described in Example 6. However, instead of soybean oil was used a purified fish oil in the same amount. The mean particle size was determined to 0.34 μm. The level of iodide in the autoclaved emulsion was 386 ppm.

Example 9

An emulsion was prepared in the same manner as described in Example 6. However, the amount of egg phospholipids was in this case reduced to 1.2 g, and the amount of cholesterol was reduced to 0.8 g per 100 ml emulsion. The mean particle size was determined to 0.34 μm.

Example 10

A mixture was prepared from the following ingredients

| | |
|---|---|
| Iodinated olive oil | 20 g |
| Phospholipids from egg | 1.2 g |
| Cholesterol | 1.0 g |
| Phenylalanine | 0.2 g |
| Glycerol | 2.25 g |
| Water for injection | to 100 ml |

A water phase was prepared by mixing of glycerol and phenylalanine with water for injection and heating of the solution to 70°-80° C.

A lipid phase was prepared by mixing of the iodinated olive oil with phospholipids and cholesterol under agitation and cautious heating, protected with nitrogen.

The lipid phase was slowly added to the water phase under vigorous mixing with a mixer type Ultraturrax. After adjustment of the pH with diluted NaOH, homogenization was performed in a valve homogenizer under high pressure. After dispensing on glass bottles the emulsion was heat sterilized at 117° C. The mean particle size of the emulsion was determined to be 0.5 μm, and the iodide concentration in the water phase was 316 ppm.

Example 11

A mixture was prepared from the following ingredients

| | |
|---|---|
| Iodinated olive oil | 20 g |
| Phospholipids from egg | 1.2 g |
| Cholesterol | 0.8 g |
| Phenylalanine | 0.2 g |
| Glycerol | 2.25 g |
| Water for injection | to 100 ml |

A water phase was prepared by mixing of glycerol, phenylalanine and phospholipids with water for injection and heating of the solution to 70°-80° C. A lipid phase was prepared by mixing of the iodinated olive oil with the cholesterol under agitation and cautious heating, protected with nitrogen. The lipid phase was slowly added to the water phase under vigorous mixing. After adjustment of the pH with diluted NaOH, homogenization was performed in a valve homogenizer under high pressure. After dispensing on glass bottles the emulsion was heat sterilized at 117° C. The mean particle size of the emulsion was determined to be 0.8 μm.

Example 12

A mixture was prepared from the following ingredients

| | |
|---|---|
| Iodinated olive oil | 10 g |
| Purified soybean oil | 10 g |
| Phospholipids from egg | 1.2 g |
| Cholesterol | 1.0 g |
| Phenylalanine | 0.2 g |
| Glycerol | 2.25 g |
| Water for injection | to 100 ml |

The emulsion was prepared in a manner analogue to that in Example 11, with a lipid phase consisting of the iodinated olive oil. the soybean oil and the cholesterol. The mean particle size of the autoclaved emulsion was determined to 0.4 μm.

Example 13

An emulsion was prepared in the same manner as described in Example 10. However, the amount of egg phospholipids was in this case increased to 1.8 g and the amount of cholesterol was increased to 1.5 g per 100 ml emulsion. The mean particle size of the emulsion was determined to 0.45 μm.

Biological Examples

Example 14

With the intention of investigating the contrast effect of the inventive emulsion, anaesthetized rats were provided surgically with a catheter in the left femoral vein. The emulsion described in Example 1 was administered in a dosage of 3 ml/kg over a period of 40 minutes and was compared with an emulsion which had been prepared without the addition of cholesterol (Intraiodol ®). The rats were sacrificed 5 minutes after completion of the infusion and the contrast effect in liver and spleen was determined by computed tomography. The inventive emulsion gave a contrast effect reaching to 98 Hounsfield units (HU) in liver and 127 HU-units in spleen (average of 4 animals), whereas the contrast effect for a corresponding emulsion which lacked a cholesterol addition (Intraiodol ®) was 81 (liver) and 72 (spleen) at the same dosage. This shows that the liver and spleen uptake of the inventive emulsion was substantially greater than the uptake of the known emulsion.

Example 15

Figure 2:
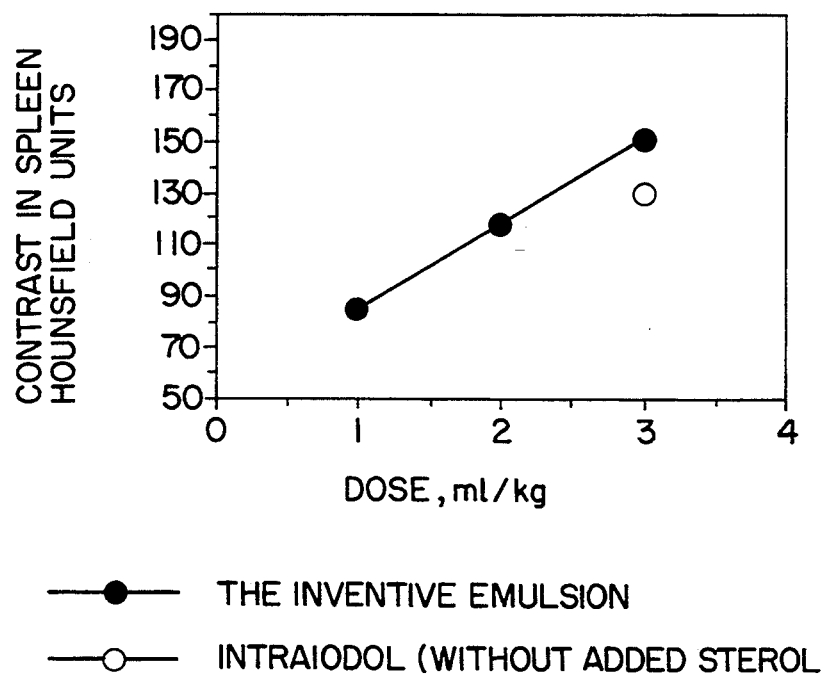
FIG. 2 illustrates contrast (measured as Hounsfield units) in the spleen of rats which had been administered with Intraiodol ® (without cholesterol additives) and an inventive emulsion in different dosages.

The contrast effect of the inventive emulsion was determined for different dosages administered to rats, with the aid of computed tomography. The emulsion defined in Example 3 was infused intravenously into a tail vein of the rat in different dosages over a period of 40 minutes. When the earlier recommended dosage of 3 ml/kg was administered, a liver uptake corresponding to 111 Hounsfield units was obtained when administering the inventive emulsion, whereas an uptake corresponding to 83 Hounsfield units was obtained when infusing corresponding cholesterol-free emulsion, Intraiodol ®. FIG. 1 shows the iodine uptake visibilized by computed tomography, where the contrast effect is shown as Hounsfield units (HU). It will be seen that a dosage of only 1 ml/kg of the inventive emulsion affords the same contrast effect in liver as 3 ml/kg of Intraiodol ®. Corresponding information for the spleen uptake is shown in FIG. 2.

This data shows that the uptake of iodized particles is substantially greater in the case of the inventive emulsion than in the case of the earlier known emulsion. Because of the higher affinity, the therapeutical index, i.e. the relation between toxic dosage and treatment dosage, also increases drastically. This effect is manifested because a sufficient contrast amplification of the liver can be achieved with a lower total dosage of contrast agent, and because the amount of contrast agent that is taken-up in sensitive organs other than the liver and the spleen is drastically reduced due to the high organ specificity of the inventive contrast medium.

Example 16

The contrast effect of an emulsion prepared in accordance with Example 4 was determined on rats with the aid of computed tomography. It was established that when this emulsion (including phytosterols) was administered in dosages of 2 ml emulsion for each kilogram of body weight, a contrast of 93 Hounsfield units in liver was obtained (n=3). By way of comparison, it can be mentioned that 87 Hounsfield units were obtained in liver when administering corresponding emulsion containing cholesterol (Example 3) in a dosage of 2 ml for each kilogram of body weight. The conclusion is that both cholesterol and phytosterols are additives which will increase the specific uptake of the emulsion in liver and spleen to generally the same extent.

Example 17

The three emulsions prepared in accordance with Example 5 (with varying quantities of cholesterol in the emulsion) were administered to rats in a dosage of 2 ml/emulsion for each kilogram of body weight over a period of 40 minutes. The X-ray density of the liver was determined with the aid of computed tomography as in Example 14, five minutes after completing the infusion. It was established that the emulsions containing respectively 0.6 and 1.2% cholesterol gave generally the same contrast effect (82 and 87 Hounsfield traits respectively, whereas the emulsion containing 0.3% cholesterol gave a contrast effect which was lower than the effect achieved with a 0.6 and 1.2% cholesterol addition (71 HU-units), and of the same order as that achieved with Intraiodol ®.

Example 18

This experiment was carried out with the intention of establishing those dosages which could be tolerated when administering the iodo emulsion prepared in accordance with Example 3 to rats by bolus injection (rapid single injection). The preparation was injected in five different dosages: 0.6, 2.4, 7.2, 21.6 and 30 ml/kg over respective periods of 10, 20, 30, 40 and 60 seconds. The rats used in the experiment had a body weight of 185–205 g. The injections were made intravenously, through a tail vein. The animals behaved normally both during and after the injections. No toxic effect was observed during the six calendar days over which the animals were monitored after the injections. The animals were killed at the end of this period, for histological examination of their internal organs. The results of the experiment showed that rats tolerate 30 ml of a 10% iodo emulsion for each kilogram of body weight when administered by bolus injection. These quantities are much greater than the quantities of emulsions that can be expected to be used in X-ray examinations (about 1 ml emulsion per kilogram of body weight). An examination of the histological liver preparations obtained, in which lipophilic substances were coloured with the dye OH Red O, showed that the emulsion particles had been essentially taken-up into the space of Disse and by the hepatocytes of the liver.

Example 19

Figure 3:
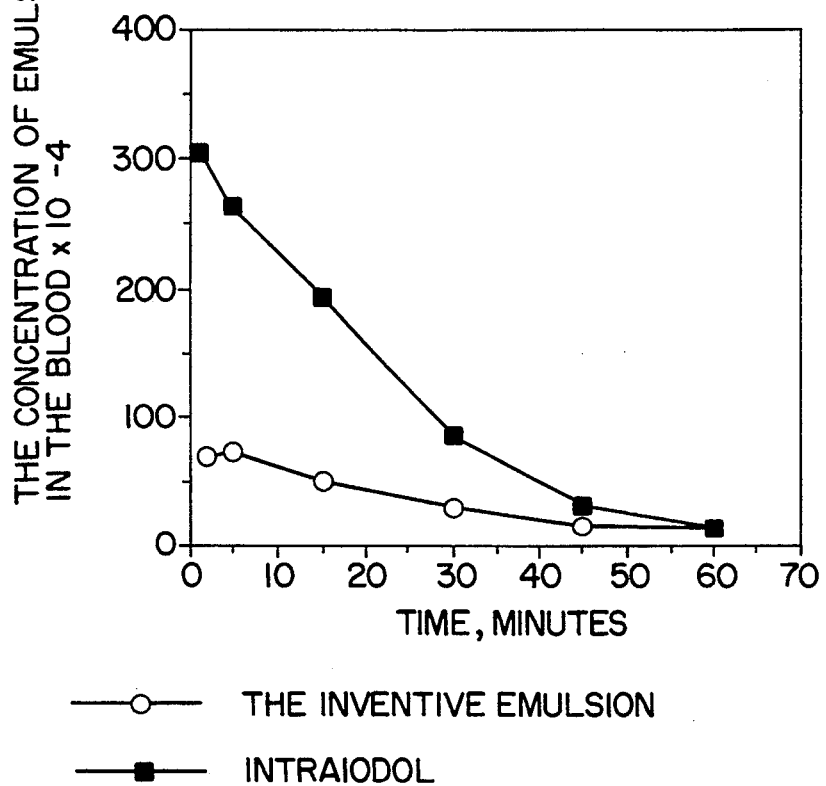
FIG. 3 illustrates the elimination of fat particles from the blood stream subsequent to the injection of Intraiodol ® (without cholesterol additives) and an inventive emulsion.

The elimination of emulsion prepared in accordance with Example 3 from the blood stream was investigated, by administering to rats intravenously in a tail vein 2.4 ml emulsion per kilogram of body weight. The concentration of emulsion in the blood was determined with a micronephelometer as the turbidity after diluting a blood sample with a physiological saline solution. For comparison purposes, a corresponding determination was made after injecting an emulsion which contained no cholesterol addition (Intraiodol ®). As will be seen from the attached diagram (FIG. 3), the amount of emulsion which remains in the blood immediately after injecting emulsion prepared in accordance with the present invention is only about ¼–⅓ of the amount that remains when a cholesterol-free emulsion is infused. This shows that the inventive emulsion is eliminated from the blood stream much more quickly than a corresponding emulsion in which no sterol has been added. In combination with the fact that the emulsion is taken-up to a great extent in the liver and the spleen, the experiment verifies that only a small quantity of the emulsion is available for uptake in other organs. This greatly reduces the possibility of side effects caused by the emulsion by influence-on other body organs.

Example 20

The tolerance of the emulsion as prepared according to Example 1 was investigated in nine dogs. The emulsion was administered in doses up to 25 ml/kg body weight. All animals survived during the period of observation of 14 days and were in good physical condition. The tolerance of the same emulsion was also investigated in a group of 6 rats after a daily administration during 7 days of 10 ml emulsion per kg body weight. The rats tolerated the emulsion well.

Example 21

For a further investigation of the contrast effect of the emulsion according to invention were rabbits used in groups of four animals per group. The emulsion according to Example 1 was administered intravenously to an ear vein with the aid of a calibrated syringe pump from SAGE instruments. The injection time was 40 minutes and the dosages 0; 1; 2 and 3 ml emulsion per kg body weight, respectively.

The rabbits were sacrificed 5 minutes after the end of the injection time and the contrast effect in the liver was determined by computed tomography. A linear relation between contrast and dose emulsion was achieved with a correlation coefficient $r^2=0.944$ and an increase in contrast of 13.8 Hounsfield units per given amount of emulsion (ml/kg body weight).

This example shows a similar contrast effect of the emulsion according to the invention both for rats and rabbits.

Example 22

The emulsion according to Example 1 was used for determining the contrast effect on anaesthetized cats. The emulsion was administered as a bolus injection (injection rate 3 ml per kg body weight and minute) in v. femoralis. The cats were sacrificed after 15 minutes and the contrast effect in the liver and the spleen was determined with the aid of computed tomography. A linear relation was observed for four animals in the interval 0–3 ml emulsion per kg body weight with the correlation coefficient $r2=0.987$. An increase in contrast effect of 16 Hounsfield units per given amount emulsion (ml per kg body weight). The example shows a similar contrast effect for rat, rabbit and cat.

Example 23

The emulsion according to Example 1 was used to determine the contrast effect in the liver of a dog with the aid of computed tomography. The dog was anaesthetized and catheterized in a peripheral vein, where the emulsion was infused during 40 minutes.

Figure 4:
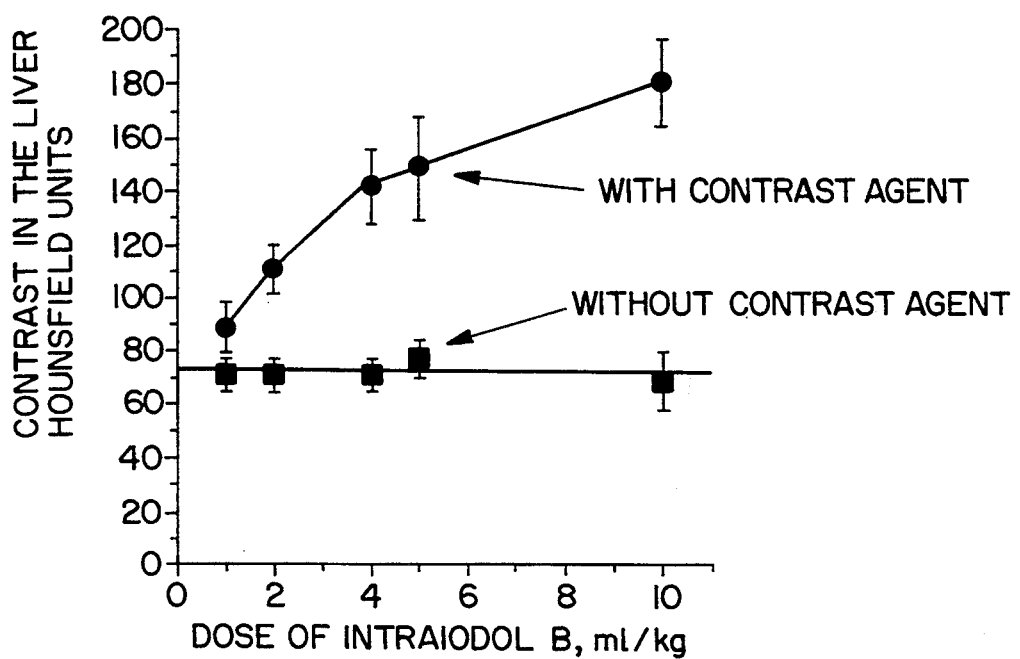
FIG. 4 illustrates the contrast effect (measured as Hounsfield units) in the liver of a dog before and after the administration of the inventive emulsion)

The emulsion was administered in the dosages 1; 2; 4; 5; and 10 ml emulsion per kg body weight, respectively, with one week interval. The contrast effect was determined immediately before the infusion (native scan) and 15 minutes after the finished infusion. FIG. 4 presents the resulting contrast in the liver and the interval for the measured results of each respective dose. It is noted that contrast effect increases essentially linear up to the dose 4 ml per kg body weight. The capability of the liver to take up higher dosages may be limited, but it can be a question of that a certain time is required for the uptake of the higher dosages of emulsion. The results show that the contrast effect of the emulsion in dogs is similar to that in previously examined species.

Example 24

The emulsion according to Example 3 was used with 0.8 g cholesterol instead of 1.2 g to examine the contrast effect in rat liver.

The emulsion was administered to unanaesthetized rats in a tail vein by means of a Braun Perfusor E infusion pump in a dose of 1 ml per kg body weight during 1 minute. The rats were sacrificed 15 (9 animals), 30 (5 animals) and 60 (5 animals) minutes after the finished infusion and examined in a computed tomograph. As a reference 3 animals were sacrificed without a preceding infusion.

The mean increase in contrast in the three groups compared to the reference was 20, 18 and 13 Hounsfield units, respectively. Thus, the contrast effect declined somewhat after a time period.

Example 25

The emulsion according to Example 3 was used with 0.8 g cholesterol instead of 1.2 g to examine the contrast effect in the liver of an anaesthetized cat. The emulsion was administered to v. femoralis in a dose of 1 ml per kg body weight during 1 minute by means of a Braun Perfusor E infusion pump. The cat was sacrificed 15 minutes later and was examined in a computed tomograph. The contrast effect was on an even level with an opacification of 74–77 Hounsfield Previous measurements on a cat exposed to comparable pharmacological tests, but not infused with contrast emulsion, resulted in a liver opacification of 61–62 Hounsfield units.

Example 26

The uptake of an emulsion of iodinated olive oil in the liver of the rats was investigated using an emulsion with a composition according to Example 10, and with a level of organically bound iodine of 4.3%. The emulsion was given to rats at a dose of 0, 1, 2 and 3 ml emulsion per kg body weight respectively, in groups of 5 rats. The emulsions were given as bolus infections in a tail vein. After one hour they were eutanized and the degree of liver opacification was evaluated using computed tomography. The results showed an increase in liver opacification of 17.7 Hounsfield Units per ml emulsion administered, with a quite linear relation ($r^2=0.977$).

In a comparison between the results obtained in Example 15, where we used an emulsion based on iodinated ethylesters of fatty acids, with a slightly higher iodine content than in this example, we obtained very similar results regarding liver opacification. We therefore conclude that also the emulsion based on iodinated triglycerides is specifically taken up in the liver of rats.

Example 27

Subacute toxicity was investigated in rats given an emulsion of iodinated olive oil, with a composition corresponding to that in Example 10, and with a level of organically bound iodine of 4.3%. The rats were operated and provided with a permanent central venous catheter. One week after the operation they were transferred to a metabolic cage and were infused for six hours at a dose rate of 10 ml emulsion per kg body weight and hour. During the infusion they soon showed some influence of the emulsion. However, after the end of the infusion they soon recovered and gained weight during the ensuing one week follow-up period.

In Example 26 it was demonstrated that a satisfactory opacification for the computed tomographic investigation of the liver of 17 Hounsfield units was obtained when 1 ml of the emulsion (with a composition as in Example 10) was given to rats. In this experiment the rats tolerated a dose of 60 ml emulsion per kg body weight. This shows that the therapeutic index of the emulsion is very high.

We claim:

1. A parental emulsion for x-ray contrast of the liver and spleen comprising at least one of each of the following:
    a) an iodized and/or brominated lipophilic substance,
    b) an emulsifier, and
    c) a cyclopenta-phenanthrene derivative
    wherein the mean droplet size of said emulsion is below $1\mu$ and the weight ratio between said emulsifier and said cyclopenta-phenanthrene derivative is between 10:1 to 1:2.

2. An emulsion according to claim 1, characterized in that the cyclopenta-phenanthrene derivative is a sterol.

3. An emulsion according to claim 1, characterized in that the emulsifier is comprised of phospholipids.

4. An emulsion according to claim 1, characterized in that the weight ratio between emulsifier and derivative in the emulsion is between 2:1 to 1:1.

5. An emulsion according to claim 1, characterized in that the lipophilic substance is comprised of iodized glycerides and/or iodized esters of fatty adds in an amount of 1–50%, of the total preparation.

6. An emulsion according to claim 5, characterized in that there is used esters of iodized fatty acids selected from the group consisting of from poppy seed oil, olive oil, peanut oil, palm oil, teaseed oil, castor oil, sesame oil, grapeseed oil, rape oil, walnut oil, corn oil, kapok oil, rice bran oil, cottonseed oil, soybean oil, safflower oil, sunflower oil, menhaden oil, salmon oil, herring oil, and lard.

7. An emulsion according to claim 5, characterized in that an ester of iodized stearic acid, oleic acid, linoleic acid or some other fatty acid has been used.

8. An emulsion according to claim 1, characterized in that it the lipid phase contains 1–50% vegetable or animal oil.

9. An emulsion according to claim 8 characterized in that the lipid phase contains iodized glycerides and non-iodized glycerides.

10. An emulsion according to claim 1, characterized in that the emulsion also includes lipophilic, pharmacologically active substances, which are specifically desired to be administered to liver and spleen.

11. An emulsion according to claim 1, characterized in that the emulsion also includes lipophilic diagnostic agents, which are desired to deliver specifically to liver and spleen.

12. An emulsion according to claim 1 characterized in that the emulsion contains at least one additional substance selected from the group consisting of monovalent weak acids, monovalent weak bases, amino acids and salts thereof.

13. An emulsion according to claim 1, characterized in that the emulsion contains additional substances, particularly monovalent weak acids, monovalent weak bases, amino acids or salts thereof.

14. An emulsion according to claim 13, characterized in that the emulsion includes one or more of the following compounds in a concentration of 0.1–5%: Glycerol, pelargonic acid, oleic acid, linoleic acid, carbamide and E-vitamin or other fat-soluble vitamins.

15. A method for preparing an emulsion according to claim 1, characterized by mixing the lipophilic, iodized and/or brominated substance and the optional additional fat or oil with the aqueous phase, the used emulsifiers, derivative of cyclopenta-phenanthrene, optional auxiliary substances and/or stability enhancing compounds, and thereafter bringing the emulsion to a mean particle size of less than 1 $\mu$m.

16. A method of carrying out examinations of the liver and/or spleen with the aid of an x-ray contrast agent in which an emulsion according to claim 1 is administered to a patient followed by imaging.

17. The emulsion of claim 2 wherein said sterol is at least one member selected from the group consisting of cholesterol, phytosterol, sitosterol, sigmasterol and campesterol.

18. The emulsion of claim 5 wherein an ester of iodized fatty acids form a vegetable or animal oil.

19. The emulsion of claim 5 wherein said amount is 5–20%.

* * * * *